United States Patent
Ralph et al.

(10) Patent No.: US 6,673,113 B2
(45) Date of Patent: *Jan. 6, 2004

(54) INTERVERTEBRAL SPACER DEVICE HAVING ARCH SHAPED SPRING ELEMENTS

(75) Inventors: James D. Ralph, Seaside Park, NJ (US); Stephen Tatar, Montvale, NJ (US); Joseph P. Errico, Kirkland, WA (US)

(73) Assignee: Spinecore, Inc., Summit, NJ (US)

( * ) Notice: Subject to any disclaimer, the term of this patent is extended or adjusted under 35 U.S.C. 154(b) by 43 days.

This patent is subject to a terminal disclaimer.

(21) Appl. No.: 09/982,148

(22) Filed: Oct. 18, 2001

(65) Prior Publication Data

US 2003/0078662 A1 Apr. 24, 2003

(51) Int. Cl.[7] .................................................. A61F 2/44
(52) U.S. Cl. ............................. 623/17.13; 623/17.14; 623/17.15; 606/61
(58) Field of Search ........................... 623/17.13–17.15; 606/61; A61F 2/44

(56) References Cited

U.S. PATENT DOCUMENTS

| | | |
|---|---|---|
| 5,458,642 A | 10/1995 | Beer et al. |
| 5,556,431 A | 9/1996 | Buttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,755,796 A | 5/1998 | Ibo et al. |
| 5,827,328 A | 10/1998 | Buttermann |
| 5,865,846 A | 2/1999 | Bryan et al. |
| 5,888,226 A | 3/1999 | Rogozinski |
| 5,893,889 A * | 4/1999 | Harrington ............... 623/17.13 |
| 5,895,428 A | 4/1999 | Berry |
| 5,899,941 A | 5/1999 | Nishijima |
| 5,989,291 A | 11/1999 | Ralph et al. |
| 6,001,130 A | 12/1999 | Bryan et al. |
| 6,019,792 A | 2/2000 | Cauthen |
| 6,039,763 A | 3/2000 | Shelokov |
| 6,063,121 A | 5/2000 | Xavier et al. |
| 6,113,637 A | 9/2000 | Gill et al. |
| 6,136,031 A | 10/2000 | Middleton |
| 6,146,421 A | 11/2000 | Gordon et al. |
| 6,156,067 A | 12/2000 | Bryan et al. |
| 6,179,874 B1 | 1/2001 | Cauthen |
| 6,228,118 B1 | 5/2001 | Gordon |
| 6,296,665 B1 * | 10/2001 | Strnad et al. ............ 623/17.16 |
| 6,368,350 B1 | 4/2002 | Erickson et al. |
| 6,468,310 B1 * | 10/2002 | Ralph et al. ............. 623/17.13 |
| 6,488,710 B2 * | 12/2002 | Besselink ................ 623/17.15 |
| 6,520,996 B1 * | 2/2003 | Manasas et al. .......... 623/23.5 |
| 2003/0083749 A1 * | 5/2003 | Kuslich et al. .......... 623/17.16 |

FOREIGN PATENT DOCUMENTS

| | | | | |
|---|---|---|---|---|
| DE | 43 15 757 C1 * | 11/1994 | ............. | A61F/2/44 |
| WO | WO 01/01893 A1 * | 1/2001 | ............. | A61F/2/44 |
| WO | WO 01/93785 A2 * | 12/2001 | ............. | A61F/2/44 |

* cited by examiner

Primary Examiner—Corrine McDermott
Assistant Examiner—Javier G. Blanco
(74) Attorney, Agent, or Firm—Joseph P. Errico, Esq.; Timothy J. Bortree, Esq.

(57) ABSTRACT

An intervertebral spacer device having a pair of opposing plates for seating against opposing vertebral bone surfaces, separated by at least one spring mechanism. The preferred spring mechanism is an arched strip spring. In a first embodiment there are multiple springs positioned independently about the area of the opposing plates. In a second embodiment there is a single arched strip spring modified to mount onto a ball-shaped head. The lower plate of this second embodiment includes a post extending upwardly from the inner surface of the plate, the post including a ball-shaped head. The spring and post members are flexibly coupled such that the upper and lower plates may rotate relative to one another.

7 Claims, 4 Drawing Sheets

INTERVERTEBRAL SPACER DEVICE HAVING ARCH SHAPED SPRING ELEMENTS

FIELD OF THE INVENTION

This invention relates generally to a spinal implant assembly for implantation into the intervertebral space between adjacent vertebral bones to simultaneously provide stabilization and continued flexibility and proper anatomical motion.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of at least one spring mechanism. This at least one spring mechanism provides a strong restoring force when a compressive load is applied to the plates, and may also permit limited rotation of the two plates relative to one another. While there are a wide variety of embodiments contemplated, two embodiment families are described herein as representative of preferred types.

More particularly, with respect to the base plates, which are largely similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates alternatively may each include outwardly directed spikes or ridges which penetrate the bone surface and mechanically hold the plates in place. However, it is more preferably anticipated that the plates should include a porous coating into which the bone of the vertebral body can grow. The most desirable upper and lower plate surface porous feature is a deflectable wire mesh into which the bone can readily grow, and which mesh will deform to seat into the concave upper and lower bone faces. (Note that this limited fusion of the bone to the base plate does not extend across the intervertebral space.) These features, while being preferred are not required.

Between the base plates, on the exterior of the device, there may also be included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopedic in conjunction with ligament and tendon repair. It is anticipated that future developments in this area will produce materials which are compatible for use with this invention, the breadth of which shall not be limited by the choice of such a material. For the purposes of this description, however, it shall be understood that such a circumferential wall is unnecessary, and in some instances may be a hindrance, and thusly is not included in the specific embodiments set forth hereinbelow.

As introduced above, the internal structure of the present invention comprises a spring member, or other equivalent subassembly which provides a restoring force when compressed. More particularly, it is desirable that the restoring forces be directed outward against the opposing plates, when a compressive load is applied to the plates. More particularly with, the restoring force providing subassembly comprises a multiplicity of arch-shaped metal strips which are secured against movement at their ends. The arched strips of metal comprise flat ends and a curvate central portion. The arched portions of the strips deflect under loading, but provide a restoring force in opposition to the loading until they are permitted to regain their original shape. The restoring force of an arched strip of metal is proportional to the elastic properties of the material as well as the length and arc of the curvate central portion of the strip. The elasticity of the metal, which endures and counteracts the strain of the material, causes a deflection in the height of the arch. In the present invention, two embodiments are contemplated: one in which there are several arched springs oriented at various positions and relative offsets to one another; and a second embodiment in which there is a single arched spring being utilized.

More particularly, with respect to the first embodiment, it is contemplated that at least one of the two base plates will include a series of spaced apart arched strip springs mounted to the plate surface at the lateral ends of the strip. The peaks of the arches are fixed by set screws or equivalent means to the opposing plate at the designed contact points. In such an embodiment, a compressive force applied to the plates at a lateral offset, or laterally asymmetric location, will cause the plates to narrow relative to one another at that location (side), while remaining spaced apart at the opposing lateral side. This is substantially equivalent to the anatomical responsiveness of the natural cartilage material present in the healthy intervertebral space.

In a second preferred embodiment of the present invention, a single arched strip spring is utilized in conjunction with a ball-shaped post which extends out from the opposing plate. This post couples to the spring at a flexible joint formed at the top thereof, which joint permits the plates to rotate relative to one another. This rotation may be constrained by the specific conformation of the joint such that the plates are free to rotate through only a range of angles. More particularly, this second embodiment comprises a pair of spaced apart base plates, one of which is simply a flat member which is approximately shaped to the shape of the vertebral bone face to which it is to be attached. The interior surface of the plate includes means for coupling a single arched spring thereto it. The other of the plates is similarly shaped, having a flat exterior surface, but further includes a short central post portion which rises out of the interior face at a nearly perpendicular angle. The top of this short post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, a single arched spring is mounted to this ball-shaped knob in such a way that it may rotate freely through a range of angles equivalent to the fraction of normal human spine rotation (to mimic normal disc rotation). In order to couple with the post, the strip spring includes an socket which accommodates the ball-shaped portion of the post. More particularly, the socket includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the arched strip spring, and the device to be rotated into the proper lordotic angulation. Subsequent introduction of the set screw into the axial bore of the post flexibly retains the head in the socket of the strip spring. This assembly provides ample spring-like performance with respect to axial compressive loads, as well as long cycle life to mimic the axial biomechanical performance of the normal human intervertebral disc.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
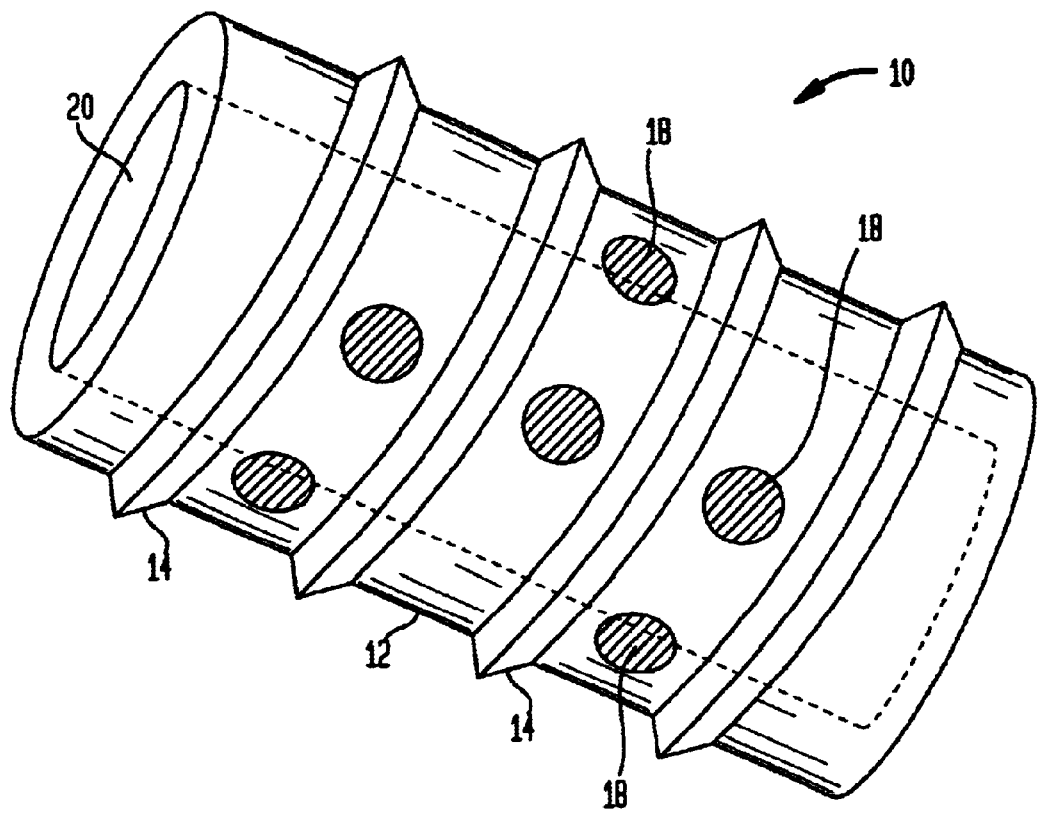
FIG. 1 is a side perspective view of an interbody fusion device of the prior art.
Figure 2:
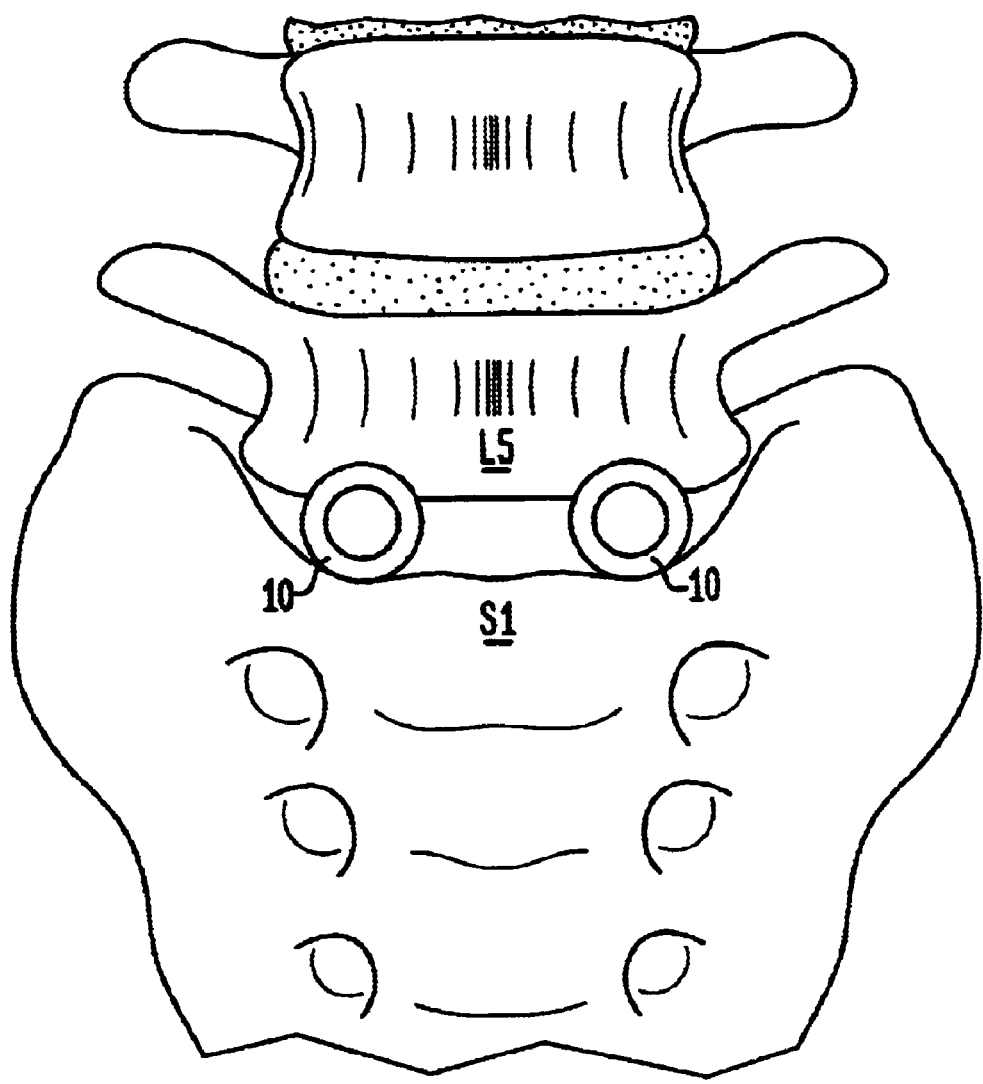
FIG. 2 is a front view of the anterior portion of the lumbo-sacral region of a human spine, into which a pair of interbody fusion devices of the type shown in FIG. 1 have been implanted.
Figure 3A:
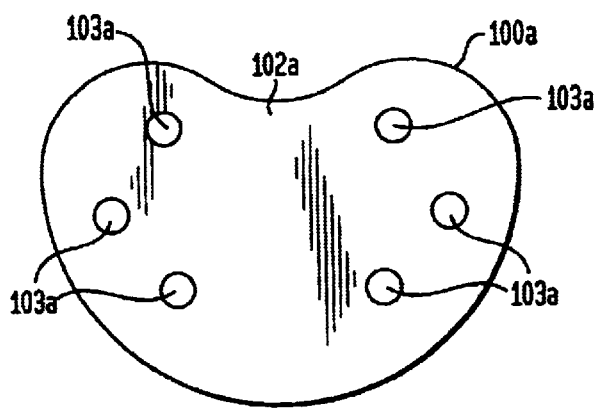
FIGS. 3a and 3b are perspective views of the upper and lower opposing plates of one embodiment of the present invention.
Figure 3B:
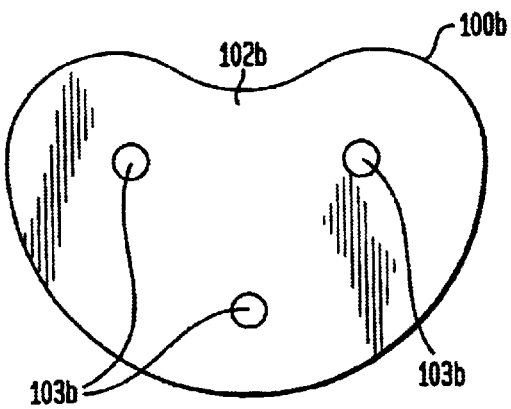

Referring now to FIGS. 3a and 3b, side cross-section views of the top and bottom plate members 100a,100b of a first embodiment of the present invention are shown. More particularly, in this embodiment, the upper and lower plates 100a,100b are nearly identical. As the device is designed to be positioned between the concave facing surfaces of adjacent vertebral bodies, the plates include substantially flat surface portions 102a,102b which seat against the opposing bone surfaces. In addition, the plates are to mate with the bone surfaces in such a way as to not rotate relative thereto. It is, therefore, preferred that the plates should include a porous coating into which the bone of the vertebral body can grow. The most desirable upper and lower plate surface porous feature is a deflectable wire mesh into which the bone can readily grow, and which mesh 104a,104b (see FIGS. 4 and 5) will deform to seat into the concave upper and lower bone faces. (Note that this limited fusion of the bone to the base plate does not extend across the intervertebral space.)

Plate 100a further includes a plurality of threaded holes 103a for receiving the set screws (shown in FIG. 5) required to affix the plurality of arched strip springs thereto it. Plate 100b correspondingly includes threaded holes 103b for similarly coupling the plate to the peaks of the arches of the strip springs.

Figure 4:
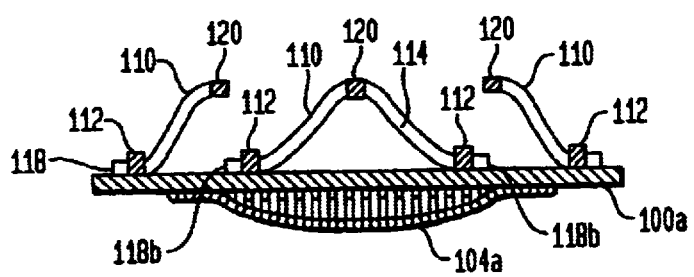
FIG. 4 is a perspective view of a lower plate having a plurality of arch-shaped strip springs mounted thereto it.
Figure 5:
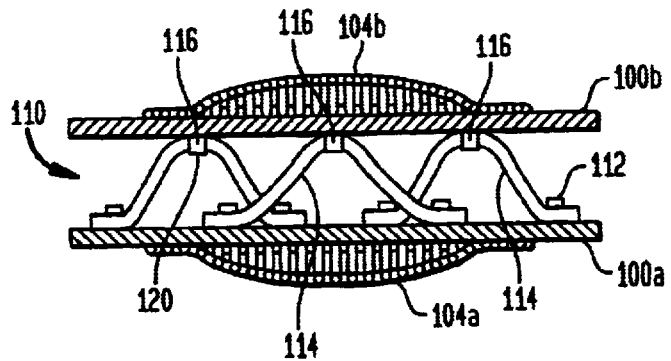
FIG. 5 is a side cross-section view of an assembled embodiment of the present invention comprising the elements shown in FIGS. 3a, 3b, and 4.

Referring now to FIGS. 4 and 5, a partially assembled embodiment of the present invention is provided in a side cross-section view, wherein the upper plates 100a illustrated in FIG. 3a includes a plurality of arched strip springs 110 attached to the plate by set screws 112. The strip springs 110 comprise flat metal members which include central arched, or curvate, portions 114 and flat end tab portions 118a,118b which may be outwardly or inwardly directed, respectively. The tab portions 118a,188b include threaded holes 120 which align with the threaded holes in the upper plate 100a so that they may be affixed thereto by set screws 112. The arched central portions 114 include a threaded hole 116 at the peak thereof. This threaded hole 116 aligns with the corresponding threaded holes of the opposing plate 100b via similar set screws (see FIG. 5).

Referring now to FIG. 5, an assembled embodiment of the present invention comprising a multiplicity of strip springs is provided in a side cross-section view. The opposing plates 100a,100b are shown as they would be disposed in the intervertebral space between two adjacent vertebral bones. The strip springs 110 are shown mounted by set screws 112 through holes 116,120 at the peak and lateral end tabs, respectively. As introduced above, the positioning and independence of the arched strip springs 100 permits the plates to deflect toward one another, and more specifically, for the overall conformation of the plates to assume parallel and non-parallel orientations as springs on one lateral side of the device deflect while the other does not.

Figure 6A:
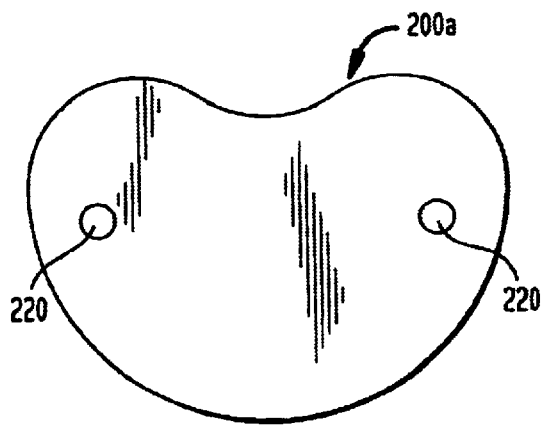
FIGS. 6a and 6b are perspective and side cross-section views, respectively of alternative upper and lower opposing plates of a second embodiment of the present invention, in which said upper plate includes a post member extending upwardly therefrom.
Figure 6B:
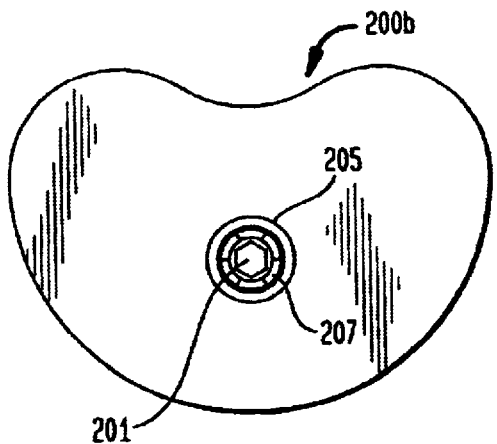

Referring now to FIGS. 6a and 6b, as well as 7 and 8, alternative upper and lower plates 200a,200b are shown in a perspective and side cross-section views, respectively. In particular, the upper plate 200a is similar to the upper plate 100b described above, inasmuch as it is designed to be positioned against a facing surface of a pair of adjacent vertebral bodies, the plate including a substantially flat surface portion 202a which seats against the bone surface. As above, it is preferred that the plate should include a porous coating or wire mesh 204a on this surface 202a into which the bone of the vertebral body can grow.

Unlike plate 100a, however, plate 200a of this second embodiment includes a single set of threaded holes 220 for receiving the set screws (shown in FIG. 8) required to affix a single arched strip spring thereto it.

Plate 200b has a similar shaped to the plates described above, i.e., having a flat exterior surface 202b which is designed to seat against the exposed opposing bone face in an intervertebral space, but plate 200b further includes a short central post member 205 which rises out of the interior face 203 at a nearly perpendicular angle. The top of this short post member 205 includes a ball-shaped head 207. The head 207 includes a central threaded axial bore 209 which extends down the post 205. This threaded bore 209 is designed to receive a small set screw 201. Prior to the insertion of the set screw 201, the ball-shaped head 207 of the post 205 can deflect radially inward (so that the ball-shaped head contracts). The insertion of the set screw 201 eliminates the capacity for this deflection.

Figure 7:
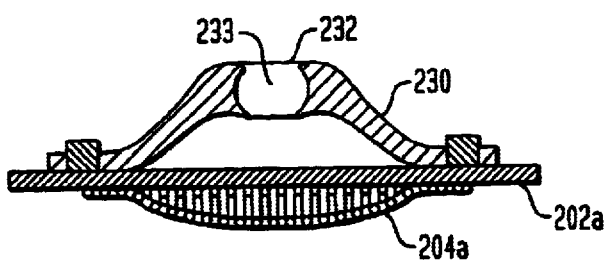
FIG. 7 is a perspective view of a lower plate having a single arch-shaped strip spring including a central socket mounted thereto it.

Referring now to FIG. 7, the arched strip spring 230 of this embodiment is shown in a side cross-section view. This arched strip spring is similar to the one utilized in the first embodiment and illustrated in the plurality in FIGS. 4 and 5, but further includes the additional feature of having an enlarged central opening 232. This central opening 232 includes a curvate volume 233 for receiving therein the ball-shaped head 207 of the post 205 of the lower plate 200b described above. More particularly, the curvate volume 233 has a substantially constant radius of curvature which is also substantially equivalent to the radius of the ball-shaped head 207 of the post 205.

Figure 8:
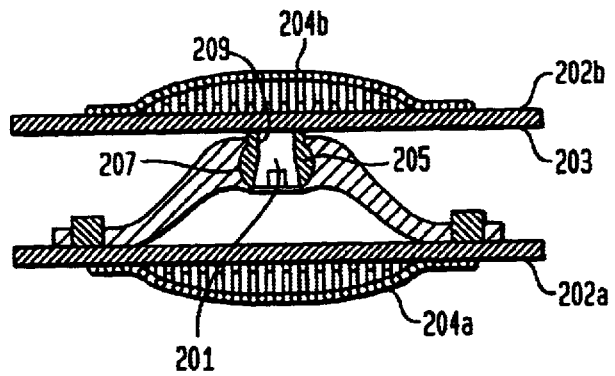
FIG. 8 is a side cross-section view of a second embodiment of the present invention which utilizes the elements shown in FIGS. 6a, 6b, and 7.

Referring also to FIG. 8, in which the fully assembled second embodiment of the present invention is shown, the combination and assembly of this embodiment is now provided. The deflectability of the ball-shaped head 207 of the post 205, prior to the insertion of the set screw 201, permits the head 207 to be inserted into the interior volume 233 at the peak of the strip spring 230. Subsequent introduction of the set screw 201 into the axial bore 209 of the post 201 flexibly couples the head 207 to the spring 230 by virtue of the head 207 not being compressible and removable from the central volume 233, but the post 205 being polyaxially retained in the socket 233. Ideally the post head 207 is locked loosely enough within the central volume 233 of the spring 230 such that anatomically relevant rotation of the plates 200*a*,200*b* remains viable. In alternative variation, however, it is possible to design the coupling such that the locking of the set screw 201 in the head 207 locks the assembly in one rotational orientation, preventing free rotation of the plates relative to one another. A combined embodiment may be one in which the set screw 201 may be selectively positioned in an unlocked (but still securing for the purpose of retention) and a locked orientation.

While there has been described and illustrated embodiments of an intervertebral spacer device, it will be apparent to those skilled in the art that variations and modifications are possible without deviating from the broad spirit and principle of the present invention. The present invention shall, therefore, not be limited solely to the specific embodiments disclosed herein.

We claim:

1. An intervertebral spacer device, comprising:

first and second plate members, each having plate surfaces thereof, said plate members being disposed in a spaced apart relationship such that inner ones of said plate surfaces oppose one another, and external ones of said plate surfaces face in opposite directions;

and at least one arched strip spring restoring force providing element disposed between the inner surfaces of said first and second plate members, said at least one arched strip spring force providing element having a peak portion between two end portions, said at least one arched strip spring force providing element being disposed such that each end portion is maintained against the inner surface of said first plate member, and such that the peak portion is maintained against the inner surface of said second plate member, and such that a compressive load applied to the external surfaces of said plate member is counteracted by said at least one restoring force providing element.

2. The device as set forth in claim 1, wherein at least one of said external surfaces of said first and second plate members comprises a porous coating.

3. The device as set forth in claim 1, wherein said second plate member further comprises a post structure rising off the inner surface thereof, and which post structure includes a ball-shaped head.

4. The device as set forth in claim 3, wherein said post structure further includes a threaded bore which extends axially from said ball-shaped head downwardly, and which bore receives therein a threaded set screw such that prior to insertion of the set screw therein, said bore permits the ball-shaped head to compress radially inwardly, and such that after the insertion of said set screw said ball-shaped head is not readily radially compressible.

5. The device as set forth in claim 4, wherein said at least one arched strip spring force providing element further comprises a central opening which includes a curvate volume for receiving and holding therein said ball-shaped head.

6. An intervertebral spacer device, comprising:

first and second plate members, each having plate surfaces thereof, said plate members being disposed in a spaced apart relationship such that inner ones of said plate surfaces oppose one another, and external ones of said plate surfaces face in opposite directions;

said second plate member further including a post structure rising off the inner surface thereof, and which post structure includes a ball-shaped head; and an arched strip spring, having a central peak portion between two end portions, said peak portion including a central opening which includes a curvate volume for receiving and holding therein said ball-shaped head, such that each end portion is maintained against the inner surface of said first plate member, and such that the peak portion is maintained against the inner surface of said second plate member, and such that a compressive load applied to the external surfaces of said plate members is counteracted by said arched strip spring.

7. The device as set forth in claim 6, wherein said post structure further comprises a threaded bore which extends axially from said ball-shaped head downwardly, and which bore receives therein a threaded set screw such that prior to insertion of the set screw therein, said bore permits the ball-shaped head to compress radially inwardly, and such that after the insertion of said set screw said ball-shaped head is not readily radially compressible.

* * * * *

UNITED STATES PATENT AND TRADEMARK OFFICE
CERTIFICATE OF CORRECTION

PATENT NO. : 6,673,113 B2
DATED : January 6, 2004
INVENTOR(S) : James D. Ralph, Stephen Tatar and Joseph P. Errico It is certified that error appears in the above-identified patent and that said Letters Patent is hereby corrected as shown below:

Column 7,
Line 34, "member" should read -- members --.

Signed and Sealed this

Eleventh Day of January, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,673,113 B1 | Page 1 of 1 |
| APPLICATION NO. | : 09/982148 | |
| DATED | : January 6, 2004 | |
| INVENTOR(S) | : James D. Ralph, Stephen Tatar and Joseph P. Errico | |

It is certified that error appears in the above-identified patent and that said Letters Patent is hereby corrected as shown below:

On the face of the patent, the residence for Stephen Tatar, should read --Montville, NJ--, not "Montvale, NJ"

Signed and Sealed this

Seventh Day of November, 2006

JON W. DUDAS
*Director of the United States Patent and Trademark Office*